(12) United States Patent
Johnston et al.

(10) Patent No.: US 9,126,125 B2
(45) Date of Patent: *Sep. 8, 2015

(54) REDUCED ENERGY ALCOHOL SEPARATION PROCESS HAVING WATER REMOVAL

(75) Inventors: Victor J. Johnston, Houston, TX (US); Radmila Jevtic, Pasadena, TX (US); David Lee, Seabrook, TX (US); Adam Orosco, Houston, TX (US); R. Jay Warner, Houston, TX (US); Heiko Weiner, Pasadena, TX (US); Zhenhua Zhou, Houston, TX (US); Emily Duff, League City, TX (US)

(73) Assignee: Celanese International Corporation, Irving, TX (US)

( * ) Notice: Subject to any disclaimer, the term of this patent is extended or adjusted under 35 U.S.C. 154(b) by 760 days.

This patent is subject to a terminal disclaimer.

(21) Appl. No.: 13/456,529

(22) Filed: Apr. 26, 2012

(65) Prior Publication Data

US 2012/0245395 A1    Sep. 27, 2012

Related U.S. Application Data

(63) Continuation-in-part of application No. 13/094,537, filed on Apr. 26, 2011, now Pat. No. 8,884,080.

(60) Provisional application No. 61/570,600, filed on Dec. 14, 2011, provisional application No. 61/363,109, filed on Jul. 9, 2010.

(51) Int. Cl.
| | |
|---|---|
| *C07C 31/08* | (2006.01) |
| *C07C 29/149* | (2006.01) |
| *C07C 29/80* | (2006.01) |
| *B01D 3/00* | (2006.01) |
| *B01D 3/14* | (2006.01) |
| *C07C 29/86* | (2006.01) |

(52) U.S. Cl.
CPC ............ *B01D 3/002* (2013.01); *B01D 3/143* (2013.01); *C07C 29/149* (2013.01); *C07C 29/80* (2013.01); *C07C 29/86* (2013.01)

(58) Field of Classification Search
CPC ........ C07C 31/08; C07C 29/149; C07C 29/80
USPC ................... 568/890, 581, 584, 585
See application file for complete search history.

(56) References Cited

U.S. PATENT DOCUMENTS

| | | |
|---|---|---|
| 2,649,407 A | 8/1953 | Harrison et al. |
| 2,702,783 A | 2/1955 | Harrison et al. |
| 3,408,267 A | 10/1968 | Miller et al. |
| 3,445,345 A | 5/1969 | Katzen et al. |
| 3,478,112 A | 11/1969 | Karl et al. |
| 3,990,952 A | 11/1976 | Katzen et al. |
| 4,275,228 A | 6/1981 | Gruffaz et al. |
| 4,306,942 A | 12/1981 | Brush et al. |
| 4,308,131 A | 12/1981 | Bannon |
| 4,317,918 A | 3/1982 | Takano et al. |
| 4,319,058 A | 3/1982 | Kulprathipanja et al. |
| 4,379,028 A | 4/1983 | Berg et al. |
| 4,395,576 A | 7/1983 | Kwantes et al. |
| 4,398,039 A | 8/1983 | Pesa et al. |
| 4,421,939 A | 12/1983 | Kiff et al. |
| 4,422,903 A | 12/1983 | Messick et al. |
| 4,454,358 A | 6/1984 | Kummer et al. |
| 4,465,854 A | 8/1984 | Pond et al. |
| 4,471,136 A | 9/1984 | Larkins et al. |
| 4,480,115 A | 10/1984 | McGinnis |
| 4,492,808 A | 1/1985 | Hagen et al. |
| 4,497,967 A | 2/1985 | Wan |
| 4,520,213 A | 5/1985 | Victor |
| 4,541,897 A | 9/1985 | Sommer et al. |
| 4,626,321 A | 12/1986 | Grethlein et al. |
| 4,678,543 A | 7/1987 | Houben et al. |
| 4,692,218 A | 9/1987 | Houben et al. |
| 4,777,303 A | 10/1988 | Kitson et al. |
| 4,804,791 A | 2/1989 | Kitson et al. |
| 4,842,693 A | 6/1989 | Wheldon |
| 4,961,826 A | 10/1990 | Grethlein et al. |
| 4,985,572 A | 1/1991 | Kitson et al. |
| 4,990,655 A | 2/1991 | Kitson et al. |

(Continued)

FOREIGN PATENT DOCUMENTS

| | | |
|---|---|---|
| CN | 201768393 | 3/2011 |
| EP | 0104197 | 4/1984 |

(Continued)

OTHER PUBLICATIONS

Office Action for Corresponding Chinese Appl. No. 201280002887.7 dated Mar. 25, 2014.

(Continued)

*Primary Examiner* — Elvis O Price
(74) *Attorney, Agent, or Firm* — Kilpatrick Townsend & Stockton LLP (57) ABSTRACT

The present invention relates to the recovery of alcohols, in particular ethanol, from a crude ethanol product obtained from the hydrogenation of acetic acid using a reduced energy process. The crude ethanol product may be fed to a distillation column in which a substantial portion of the water is removed with the acetic acid in the residue. Additional water may be removed by using a pressure swing adsorption unit, molecular sieve, and/or membrane. Ethanol extraction may also be used to reduce the ethanol concentration in the recycle streams.

22 Claims, 2 Drawing Sheets

(56) References Cited

U.S. PATENT DOCUMENTS

| | | | |
|---|---|---|---|
| 5,035,776 | A | 7/1991 | Knapp |
| 5,061,671 | A | 10/1991 | Kitson et al. |
| 5,124,004 | A | 6/1992 | Grethlein et al. |
| 5,149,680 | A | 9/1992 | Kitson et al. |
| 5,185,481 | A | 2/1993 | Muto et al. |
| 5,215,902 | A | 6/1993 | Tedder |
| 5,227,141 | A | 7/1993 | Kim et al. |
| 5,233,099 | A | 8/1993 | Tabata et al. |
| 5,237,108 | A | 8/1993 | Marraccini et al. |
| 5,250,271 | A | 10/1993 | Horizoe et al. |
| 5,348,625 | A | 9/1994 | Berg |
| 5,415,741 | A | 5/1995 | Berg |
| 5,437,770 | A | 8/1995 | Berg |
| 5,445,716 | A | 8/1995 | Berg |
| 5,449,440 | A | 9/1995 | Rescalli et al. |
| 5,762,765 | A | 6/1998 | Berg |
| 5,770,770 | A | 6/1998 | Kim et al. |
| 5,800,681 | A | 9/1998 | Berg |
| 5,993,610 | A | 11/1999 | Berg |
| 6,121,498 | A | 9/2000 | Tustin et al. |
| 6,294,703 | B1 | 9/2001 | Hara et al. |
| 6,375,807 | B1 | 4/2002 | Nieuwoudt et al. |
| 6,509,180 | B1 | 1/2003 | Verser et al. |
| 6,693,213 | B1 | 2/2004 | Kolena et al. |
| 6,723,886 | B2 | 4/2004 | Allison et al. |
| 6,906,228 | B2 | 6/2005 | Fischer et al. |
| 6,927,048 | B2 | 8/2005 | Verser et al. |
| 7,297,236 | B1 | 11/2007 | Vander Griend et al. |
| 7,399,892 | B2 | 7/2008 | Rix et al. |
| 7,507,562 | B2 | 3/2009 | Verser et al. |
| 7,553,397 | B1 | 6/2009 | Colley et al. |
| 7,572,353 | B1 | 8/2009 | Vander et al. |
| 7,608,744 | B1 | 10/2009 | Johnston et al. |
| 7,732,173 | B2 | 6/2010 | Mairal et al. |
| 7,744,727 | B2 | 6/2010 | Blum et al. |
| 7,842,844 | B2 | 11/2010 | Atkins |
| 2006/0019360 | A1 | 1/2006 | Verser et al. |
| 2006/0127999 | A1 | 6/2006 | Verser et al. |
| 2007/0270511 | A1 | 11/2007 | Melnichuk et al. |
| 2008/0135396 | A1 | 6/2008 | Blum |
| 2008/0193989 | A1 | 8/2008 | Verser et al. |
| 2008/0210540 | A1 | 9/2008 | Dieterle |
| 2009/0014313 | A1 | 1/2009 | Lee et al. |
| 2009/0023192 | A1 | 1/2009 | Verser et al. |
| 2009/0081749 | A1 | 3/2009 | Verser et al. |
| 2009/0166172 | A1 | 7/2009 | Casey et al. |
| 2009/0318573 | A1 | 12/2009 | Stites et al. |
| 2010/0029980 | A1 | 2/2010 | Johnston et al. |
| 2010/0029995 | A1 | 2/2010 | Johnston et al. |
| 2010/0121114 | A1 | 5/2010 | Johnston et al. |
| 2011/0082322 | A1 | 4/2011 | Jevtic et al. |
| 2011/0190532 | A1 | 8/2011 | Johnston et al. |
| 2011/0190549 | A1 | 8/2011 | Horton et al. |
| 2012/0010437 | A1 | 1/2012 | Jevtic |
| 2012/0010438 | A1 | 1/2012 | Lee et al. |
| 2012/0010439 | A1 | 1/2012 | Jevtic et al. |
| 2012/0010440 | A1 | 1/2012 | Sarager |
| 2012/0010445 | A1 | 1/2012 | Johnston et al. |
| 2012/0010447 | A1 | 1/2012 | Warner et al. |
| 2012/0273338 | A1 | 11/2012 | Lee |
| 2012/0277481 | A1 | 11/2012 | Warner |

FOREIGN PATENT DOCUMENTS

| | | |
|---|---|---|
| EP | 0137749 | 4/1985 |
| EP | 0167300 | 1/1986 |
| EP | 0456647 | 11/1991 |
| EP | 1614458 | 1/2006 |
| EP | 2060553 | 5/2009 |
| EP | 2060555 | 5/2009 |
| EP | 2072487 | 6/2009 |
| EP | 2072488 | 6/2009 |
| EP | 2072489 | 6/2009 |
| EP | 2072492 | 6/2009 |
| EP | 2186787 | 5/2010 |
| JP | 4-193304 | 7/1992 |
| WO | WO 83/03409 | 10/1983 |
| WO | WO 2008/135192 | 11/2008 |
| WO | WO 2009/009322 | 1/2009 |
| WO | WO 2009/009323 | 1/2009 |
| WO | WO 2009/048335 | 4/2009 |
| WO | WO 2009/063176 | 5/2009 |
| WO | WO 2010/055285 | 5/2010 |
| WO | WO 2011/097190 | 8/2011 |
| WO | WO 2011/097211 | 8/2011 |
| WO | WO 2011/097220 | 8/2011 |
| WO | WO 2011/097227 | 8/2011 |
| WO | WO 2011/140457 | 11/2011 |
| WO | WO 2012/006228 | 1/2012 |

OTHER PUBLICATIONS

Zheng, et al. (2007). Preparation and catalytic properties of a bimetallic Sn—Pt complex in the supercages of NaY zeolite by use of surface organometallic chemistry, Applied Organometallic Chemistry, 21(10), 836-840.

ZeaChem, Inc., Technology Overview, Lakewood, Colorado www.zeachem.com, 2008.

Santori et al.(2000). Hydrogenation of carbonylic compounds on Pt/SiO2 catalysts modified with SnBu4, Studies in Surface Science and Catalysis, 130, 2063-2068.

Rachmady, Acetic Acid Reduction by H2 on Bimetallic Pt—Fe Catalysts, Journal of Catalysis 209, 87-98 (Apr. 1, 2002), Elsevier Science (USA).

Pallasana et al., Reaction Paths in the Hydrogenolysis of Acetic Acid to Ethanol over Pd(111), Re(0001), and RdRe Alloys, Journal of Catalysis 209, 289-305 Mar. 1, 2002.

Hilmen, Separation of Azeotropic Mixtures: Tools for Analysis and Studies on Batch Distillation Operation (Nov. 2000) p. 17-20.

Gursahani et al., Reaction kinetics measurements and analysis of reaction pathways for conversions of acetic acid, ethanol, and ethyl acetate over silica-supported Pt, Applied Catalysis A: General 222 (2001) 369-392.

Amit M. Goda et al., DFT modeling of selective reduction of acetic acid to acetaldehyde on Pt-based bimetallic catalysts, 20th NAM, Houston, TX, Jun. 17-22, 2007 available online at <http://www.nacatsoc.org/20nam/abstracts/O-S9-18.pdf>.

Alcala, et al., (2005). Experimental and DFT studies of the conversion of ethanol and acetic acid on PtSn-based catalysts, Journal of Physical Chemistry, 109(6), 2074-2085.

Yu Huang, et al., "Low-Energy Distillation-Membrane separation Process", Industrial & Engineering Chemistry Research, Am. Chem. Soc., vol. 49, No. 8, Jan. 1, 2010, pp. 3760-3768.

International Search Report and Written Opinion for PCT/US2011/042753 mailed on Dec. 5, 2011.

International Written Opinion for PCT/US2011/042753 mailed Jul. 16, 2012.

International Search Report and Written Opinion for PCT/US2012/035183 mailed Jun. 14, 2012.

Response to Final Office Action for U.S. Appl. No. 13/094,488, filed Oct. 18, 2013.

Response to Final Office Action for U.S. Appl. No. 13/094,610, filed Oct. 18, 2013.

Response to Final Office Action for U.S. Appl. No. 13/094,688, filed Nov. 25, 2013.

Response to Final Office Action for U.S. Appl. No. 13/094,661, filed Nov. 25, 2013.

International Preliminary Report on Patentability for PCT/US2012/035183 mailed Nov. 7, 2013.

Office Action for Chinese Appl. No. 201280002887.7 dated Dec. 3, 2014.

International Preliminary Report on Patentability for PCT/US2011/042753 mailed Oct. 22, 2012.

REDUCED ENERGY ALCOHOL SEPARATION PROCESS HAVING WATER REMOVAL

CROSS REFERENCE TO RELATED APPLICATIONS

This application claims priority to U.S. Provisional App. No. 61/570,600, filed on Dec. 14, 2011, the entirety of which is incorporated herein by reference. This application also is a continuation-in-part U.S. App. No. 13/094,537, filed on Apr. 26, 2011, which claims priority to U.S. Provisional App. No. 61/363,109, filed on Jul. 9, 2010, the entirety of which is incorporated herein by reference.

FIELD OF THE INVENTION

The present invention relates generally to processes for producing alcohols and, in particular, to a reduced energy process for recovering ethanol that have a water removal step.

BACKGROUND OF THE INVENTION

Ethanol for industrial use is conventionally produced from organic feed stocks, such as petroleum oil, natural gas, or coal, from feed stock intermediates, such as syngas, or from starchy materials or cellulose materials, such as corn or sugar cane. Conventional methods for producing ethanol from organic feed stocks, as well as from cellulose materials, include the acid-catalyzed hydration of ethylene, methanol homologation, direct alcohol synthesis, and Fischer-Tropsch synthesis. Instability in organic feed stock prices contributes to fluctuations in the cost of conventionally produced ethanol, making the need for alternative sources of ethanol production all the greater when feed stock prices rise. Starchy materials, as well as cellulosic materials, are converted to ethanol by fermentation. However, fermentation is typically used for consumer production of ethanol, which is suitable for fuels or human consumption. In addition, fermentation of starchy or cellulosic materials competes with food sources and places restraints on the amount of ethanol that can be produced for industrial use.

Ethanol production via the reduction of alkanoic acids and/or other carbonyl group-containing compounds has been widely studied, and a variety of combinations of catalysts, supports, and operating conditions have been mentioned in the literature. During the reduction of alkanoic acid, e.g., acetic acid, other compounds are formed with ethanol or are formed in side reactions. These impurities limit the production and recovery of ethanol from such reaction mixtures. For example, during hydrogenation, esters are produced that together with ethanol and/or water form azeotropes, which are difficult to separate. In addition when conversion is incomplete, unreacted acid remains in the crude ethanol product, which must be removed to recover ethanol.

EP02060553 describes a process for converting hydrocarbons to ethanol involving converting the hydrocarbons to ethanoic acid and hydrogenating the ethanoic acid to ethanol. The stream from the hydrogenation reactor is separated to obtain an ethanol stream and a stream of acetic acid and ethyl acetate, which is recycled to the hydrogenation reactor.

U.S. Pat. No. 7,842,844 describes a process for improving selectivity and catalyst activity and operating life for the conversion of hydrocarbons to ethanol and optionally acetic acid in the presence of a particulate catalyst, said conversion proceeding via a syngas generation intermediate step.

The need remains for improving the recovery of ethanol from a crude product obtained by reducing alkanoic acids, such as acetic acid, and/or other carbonyl group-containing compounds.

SUMMARY OF THE INVENTION

In a first embodiment, the present invention is directed to a process for producing ethanol, comprising the steps of hydrogenating acetic acid from an acetic acid feed stream in a reactor to form a crude ethanol product comprising ethanol, ethyl acetate, acetic acid, and water, separating at least a portion of the crude ethanol product in a column into a first distillate comprising ethanol, ethyl acetate, and at least 5 wt. % water, and a first residue comprising acetic acid and water, wherein a substantial portion of the water in the crude ethanol product that is fed to the column is removed in the first residue, separating at least a portion of the first distillate in a second distillation column into a second residue comprising ethanol and water, and a second distillate comprising ethyl acetate, and removing water from the second residue using a water removal unit selected from the group consisting of an adsorption unit, membrane, molecular sieves, and combinations thereof, to form the ethanol product stream, provided that no water is removed from the first distillate prior to the second distillation column. In one embodiment from 30 to 90% of the water, and preferably at least 50%, in the crude ethanol product is removed in the first residue stream. A vapor portion of the second residue may be fed to the water removal unit.

In a second embodiment, the present invention is directed to a process for producing ethanol, comprising the steps of providing a crude ethanol product comprising ethanol, ethyl acetate, acetic acid, and water; separating at least a portion of the crude ethanol product in a column into a first distillate comprising ethanol, ethyl acetate, and at least 5 wt. % water, and a first residue comprising acetic acid and water, wherein a substantial portion of the water in the crude ethanol product that is fed to the column is removed in the first residue; separating at least a portion of the first distillate in a second distillation column into a second residue comprising ethanol and water, and a second distillate comprising ethyl acetate; and removing water from the second residue using a water removal unit selected from the group consisting of an adsorption unit, membrane, molecular sieves, and combinations thereof, to form the ethanol product stream, provided that no water is removed from the first distillate prior to the second distillation column.

In a third embodiment, the present invention is directed to a process for producing ethanol, comprising the steps of hydrogenating acetic acid from an acetic acid feed stream in a reactor to form a crude ethanol product comprising ethanol, ethyl acetate, acetic acid, and water; separating at least a portion of the crude ethanol product in a column into a first distillate comprising ethanol, ethyl acetate, and at least 5 wt. % water, and a first residue comprising acetic acid and water, wherein a substantial portion of the water in the crude ethanol product that is fed to the column is removed in the first residue; separating at least a portion of the first distillate in a second distillation column into a second residue comprising ethanol and water, and a second distillate comprising ethyl acetate; and removing water from a vapor portion of the second residue using a water removal unit selected from the group consisting of an adsorption unit, membrane, molecular sieves, and combinations thereof, to form the ethanol product stream.

In a fourth embodiment, the present invention is directed to a process for producing ethanol, comprising the steps of hydrogenating acetic acid from an acetic acid feed stream in a reactor to form a crude ethanol product comprising ethanol, ethyl acetate, acetic acid, and water; separating at least a portion of the crude ethanol product in a column into a first distillate comprising ethanol, ethyl acetate, and at least 5 wt. % water, and a first residue comprising acetic acid and water, wherein a substantial portion of the water in the crude ethanol product that is fed to the column is removed in the first residue, separating at least a portion of the first distillate in a second distillation column into a second residue comprising ethanol and water, and a second distillate comprising ethyl acetate and ethanol, and extracting ethanol from the second distillate to provide a raffinate that is deficient in ethanol. In one embodiment, the raffinate is returned to the reactor and may have ethanol concentration, e.g., less than 2 wt. %, that is less than the ethanol concentration of the second distillate.

BRIEF DESCRIPTION OF DRAWINGS

The invention is described in detail below with reference to the appended drawings, wherein like numerals designate similar parts.

DETAILED DESCRIPTION OF THE INVENTION

Introduction

The present invention relates to processes for recovering ethanol produced by hydrogenating acetic acid in the presence of a catalyst. The hydrogenation reaction produces a crude ethanol product that comprises ethanol, water, ethyl acetate, unreacted acetic acid, and other impurities. To improve operating efficiencies, the processes of the present invention involve separating the crude ethanol product into a residue stream comprising water and acetic acid and a distillate stream comprising ethanol. Additional organic impurities are separated from the distillate stream in a subsequent column and ethanol is recovered in the bottom of that column along with water. In embodiments of the present invention, the water is removed using a water removal unit selected from the group consisting of an adsorption unit, membrane, molecular sieves, and combinations thereof. Preferably, the feed to the water removal unit is from a portion of the vapor return of the reboiler on the light ends column. Advantageously, this separation approach results in reducing energy requirements to recover ethanol from the crude ethanol product.

For purposes of the present invention, it is advantageous to remove water from the produced ethanol once the acetic acid and organic impurities are removed. Although some water may be removed with the acetic acid and organic impurities it is preferred to remove water from ethanol in a final step. The water separation unit may remove at least 75% of the water from the vapor return of the reboiler, e.g., at least 80% or at least 90%. The dried ethanol obtained from the water separation unit may be suitable as an industrial ethanol or as a fuel-grade ethanol that is suitable for blending with gasoline. The dried ethanol may comprise less than 8 wt. % water, e.g., less than 4 wt. % water, less than 3 wt. % water or less than 1 wt. % water.

In recovering ethanol, the processes of the present invention use one or more distillation columns. Unreacted acetic acid is removed from the crude ethanol product in the residue stream of the initial (first) column to reduce esterification that would consume the desired ethanol product. In preferred embodiments, the residue stream comprises a substantial portion of the water and the unreacted acetic acid from the crude ethanol product. In one embodiment, the initial column is operated so that minor amounts of, preferably no, acetic acid is carried over in the distillate and minor amounts of, preferably no, ethanol is leaked into the residue. The substantial portion of the water removed in the residue may vary depending on the composition of the crude ethanol product, which is a result of the acetic acid conversion and selectivity to ethanol. In one embodiment, 30 to 90% of the water in the crude ethanol product is removed in the residue, e.g., from 40 to 88% of the water or from 50 to 84% of the water. Removing less water in the residue may increase acetic acid carry over in the distillate. In addition, leaving too much water in the residue may also cause increases in ethanol leakage into the residue. Also, depending on the conversion, the energy requirement may also increase when too much water is left in the distillate.

Preferably, a majority of the water in the crude ethanol product that is fed to the column may be removed in the first residue, for example, up to about 90% of the water from the crude ethanol product, and more preferably up to about 75%. In some embodiments, with lower conversions of acetic acid and/or selectivity, the substantial portion of water withdrawn as in the residue may be from 30% to 80%, e.g., from 40% to 75%.

In an exemplary embodiment, the energy requirements by the initial column in the process according to the present invention may be less than 5.5 MMBtu per ton of refined ethanol, e.g., less than 4.5 MMBtu per ton of refined ethanol or less than 3.5 MMBtu per ton of refined ethanol. In some embodiments, the process may operate with higher energy requirements provided that the total energy requirement is less than the energy required to remove most of the water from the crude ethanol product in the distillate, e.g. more than 65% of the water in the crude ethanol product. Additional energy is required to operate an initial column that removes more water in either the distillate and/or residue. The energy requirements for the initial column may increase rapidly when the water concentration in the distillate approaches the azeotropic amount, e.g., from about 4 wt. % to about 7 wt. %. To achieve these low water concentrations an increase of the reflux ratio is required and results in an increase of the energy demands on the column. For example, removing additional water, so that more than 90% of the water is removed in the residue, requires a high reflux ratio of greater than 5:1, greater than 10:1 or greater than 30:1. This may place additional energy demands on the distillation column.

The residue stream may comprise at least 85% of the acetic acid from the crude ethanol product, e.g., at least 90% and more preferably at least about 100%. In terms of ranges, the residue stream preferably comprises from 85% to 100% of the unreacted acetic acid from the crude ethanol product, and more preferably from 90% to 100%. In one embodiment, substantially all of the unreacted acetic acid is recovered in the residue stream. By removing substantially all of the unreacted acetic acid from the crude ethanol product, the process, in some aspects, does not require further separation of acetic acid from the ethanol product. In this aspect, the ethanol product may contain some acetic acid, e.g., trace amounts of acetic acid.

The composition of the residue stream may vary depending on acetic acid conversion, as discussed below, as well as the composition of the crude ethanol product and separation conditions in the first column. Depending on the composition, the residue stream may be: (i) entirely or partially recycled to the hydrogenation reactor, (ii) separated into acid and water streams, (iii) treated with a solvent in a weak acid recovery process, (iv) reacted with an alcohol to consume the unreacted acetic acid, or (v) disposed to a waste water treatment facility.

In another embodiment, it is also advantageous to remove ethanol from the recycle streams. This reduces the amount of ethanol being passing over the catalyst and thus may increase the capacity to hydrogenate carboxylic acid and/or ethyl acetate. A recycle stream that comprises ethanol may be fed to an extractive separation unit to extract ethanol and the raffinate may be fed to the reactor. The extract ethanol may be combined with the dried ethanol obtained from the water separation to increase overall ethanol recovery. In one embodiment, at least 80% of the ethanol in the recycle stream is recovered, and more preferably at least 90%. Thus, the overall ethanol recovery may be greater than 90%, e.g., greater than 95%.

The process of the present invention may be used with any hydrogenation process for producing ethanol. The materials, catalysts, reaction conditions, and separation processes that may be used in the hydrogenation of acetic acid are described further below.

The raw materials, acetic acid and hydrogen, used in connection with the process of this invention may be derived from any suitable source including natural gas, petroleum, coal, biomass, and so forth. As examples, acetic acid may be produced via methanol carbonylation, acetaldehyde oxidation, ethane oxidation, oxidative fermentation, and anaerobic fermentation. Methanol carbonylation processes suitable for production of acetic acid are described in U.S. Pat. Nos. 7,208,624; 7,115,772; 7,005,541; 6,657,078; 6,627,770; 6,143,930; 5,599,976; 5,144,068; 5,026,908; 5,001,259; and 4,994,608, the entire disclosures of which are incorporated herein by reference. Optionally, the production of ethanol may be integrated with such methanol carbonylation processes.

As petroleum and natural gas prices fluctuate becoming either more or less expensive, methods for producing acetic acid and intermediates such as methanol and carbon monoxide from other carbon sources have drawn increasing interest. In particular, when petroleum is relatively expensive, it may become advantageous to produce acetic acid from synthesis gas ("syngas") that is derived from more available carbon sources. U.S. Pat. No. 6,232,352, the entirety of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syngas is diverted from the methanol synthesis loop and supplied to a separator unit to recover CO, which is then used to produce acetic acid. In a similar manner, hydrogen for the hydrogenation step may be supplied from syngas.

In some embodiments, some or all of the raw materials for the above-described acetic acid hydrogenation process may be derived partially or entirely from syngas. For example, the acetic acid may be formed from methanol and carbon monoxide, both of which may be derived from syngas. The syngas may be formed by partial oxidation reforming or steam reforming, and the carbon monoxide may be separated from syngas. Similarly, hydrogen that is used in the step of hydrogenating the acetic acid to form the crude ethanol product may be separated from syngas. The syngas, in turn, may be derived from a variety of carbon sources. The carbon source, for example, may be selected from the group consisting of natural gas, oil, petroleum, coal, biomass, and combinations thereof. Syngas or hydrogen may also be obtained from bio-derived methane gas, such as bio-derived methane gas produced by landfills or agricultural waste.

Biomass-derived syngas has a detectable $^{14}C$ isotope content as compared to fossil fuels such as coal or natural gas. An equilibrium forms in the Earth's atmosphere between constant new formation and constant degradation, and so the proportion of the $^{14}C$ nuclei in the carbon in the atmosphere on Earth is constant over long periods. The same distribution ratio $n^{14}C:n^{12}C$ ratio is established in living organisms as is present in the surrounding atmosphere, which stops at death and $^{14}C$ decomposes at a half life of about 6000 years. Methanol, acetic acid and/or ethanol formed from biomass-derived syngas would be expected to have a $^{14}C$ content that is substantially similar to living organisms. For example, the $^{14}C:^{12}C$ ratio of the methanol, acetic acid and/or ethanol may be from one half to about 1 of the $^{14}C:^{12}C$ ratio for living organisms. In other embodiments, the syngas, methanol, acetic acid and/or ethanol described herein are derived wholly from fossil fuels, i.e. carbon sources produced over 60,000 years ago, may have no detectable $^{14}C$ content.

In another embodiment, the acetic acid used in the hydrogenation step may be formed from the fermentation of biomass. The fermentation process preferably utilizes an acetogenic process or a homoacetogenic microorganism to ferment sugars to acetic acid producing little, if any, carbon dioxide as a by-product. The carbon efficiency for the fermentation process preferably is greater than 70%, greater than 80% or greater than 90% as compared to conventional yeast processing, which typically has a carbon efficiency of about 67%. Optionally, the microorganism employed in the fermentation process is of a genus selected from the group consisting of *Clostridium, Lactobacillus, Moorella, Thermoanaerobacter, Propionibacterium, Propionispera, Anaerobiospirillum*, and *Bacteriodes*, and in particular, species selected from the group consisting of *Clostridium formicoaceticum, Clostridium butyricum, Moorella thermoacetica, Thermoanaerobacter kivui, Lactobacillus delbrukii, Propionibacterium acidipropionici, Propionispera arboris, Anaerobiospirillum succinicproducens, Bacteriodes amylophilus* and *Bacteriodes ruminicola*. Optionally, in this process, all or a portion of the unfermented residue from the biomass, e.g., lignans, may be gasified to form hydrogen that may be used in the hydrogenation step of the present invention. Exemplary fermentation processes for forming acetic acid are disclosed in U.S. Pat. No. 6,509,180 and U.S. Pub. Nos. 2008/0193989 and 2009/0281354, the entireties of which are incorporated herein by reference.

Examples of biomass include, but are not limited to, agricultural wastes, forest products, grasses, and other cellulosic material, timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth. Another biomass source is black liquor, which is an aqueous solution of lignin residues, hemicellulose, and inorganic chemicals.

U.S. Pat. No. RE 35,377, also incorporated herein by reference, provides a method for the production of methanol by conversion of carbonaceous materials such as oil, coal, natural gas and biomass materials. The process includes hydro-gasification of solid and/or liquid carbonaceous materials to obtain a process gas which is steam pyrolyzed with additional natural gas to form syngas. The syngas is converted to methanol which may be carbonylated to acetic acid. The method likewise produces hydrogen which may be used in connection with this invention as noted above. U.S. Pat. No. 5,821,111, which discloses a process for converting waste biomass through gasification into synthesis gas, and U.S. Pat. No. 6,685,754, which discloses a method for the production of a hydrogen-containing gas composition, such as a syngas including hydrogen and carbon monoxide, are incorporated herein by reference in their entireties.

Acetic acid fed to the hydrogenation reactor may also comprise other carboxylic acids and anhydrides, as well as acetaldehyde and acetone. Preferably, a suitable acetic acid feed stream comprises one or more of the compounds selected from the group consisting of acetic acid, acetic anhydride, acetaldehyde, ethyl acetate, and mixtures thereof. These other compounds may also be hydrogenated in the processes of the present invention. In some embodiments, the presence of carboxylic acids, such as propanoic acid or its aldehyde, may be beneficial in producing propanol. Water may also be present in the acetic acid feed.

Alternatively, acetic acid in vapor form may be taken directly as crude product from the flash vessel of a methanol carbonylation unit of the class described in U.S. Pat. No. 6,657,078, the entirety of which is incorporated herein by reference. The crude vapor product, for example, may be fed directly to the ethanol synthesis reaction zones of the present invention without the need for condensing the acetic acid and light ends or removing water, saving overall processing costs.

The acetic acid may be vaporized at the reaction temperature, following which the vaporized acetic acid may be fed along with hydrogen in an undiluted state or diluted with a relatively inert carrier gas, such as nitrogen, argon, helium, carbon dioxide and the like. For reactions run in the vapor phase, the temperature should be controlled in the system such that it does not fall below the dew point of acetic acid. In one embodiment, the acetic acid may be vaporized at the boiling point of acetic acid at the particular pressure, and then the vaporized acetic acid may be further heated to the reactor inlet temperature. In another embodiment, the acetic acid is mixed with other gases before vaporizing, followed by heating the mixed vapors up to the reactor inlet temperature. Preferably, the acetic acid is transferred to the vapor state by passing hydrogen and/or recycle gas through the acetic acid at a temperature at or below 125° C., followed by heating of the combined gaseous stream to the reactor inlet temperature.

Some embodiments of the process of hydrogenating acetic acid to form ethanol may include a variety of configurations using a fixed bed reactor or a fluidized bed reactor. In many embodiments of the present invention, an "adiabatic" reactor can be used; that is, there is little or no need for internal plumbing through the reaction zone to add or remove heat. In other embodiments, a radial flow reactor or reactors may be employed, or a series of reactors may be employed with or without heat exchange, quenching, or introduction of additional feed material. Alternatively, a shell and tube reactor provided with a heat transfer medium may be used. In many cases, the reaction zone may be housed in a single vessel or in a series of vessels with heat exchangers therebetween.

In preferred embodiments, the catalyst is employed in a fixed bed reactor, e.g., in the shape of a pipe or tube, where the reactants, typically in the vapor form, are passed over or through the catalyst. Other reactors, such as fluid or ebullient bed reactors, can be employed. In some instances, the hydrogenation catalysts may be used in conjunction with an inert material to regulate the pressure drop of the reactant stream through the catalyst bed and the contact time of the reactant compounds with the catalyst particles.

The hydrogenation reaction may be carried out in either the liquid phase or vapor phase. Preferably, the reaction is carried out in the vapor phase under the following conditions. The reaction temperature may range from 125° C. to 350° C., e.g., from 200° C. to 325° C., from 225° C. to 300° C., or from 250° C. to 300° C. The pressure may range from 10 kPa to 3000 kPa, e.g., from 50 kPa to 2300 kPa, or from 100 kPa to 2100 kPa. The reactants may be fed to the reactor at a gas hourly space velocity (GHSV) from 50 $hr^{-1}$ to 50,000 $hr^{-1}$, e.g., from 500 $hr^{-1}$ to 30,000 $hr^{-1}$, from 1000 $hr^{-1}$ to 10,000 $hr^{-1}$, or from 1000 $hr^{-1}$ to 6500 $hr^{-1}$.

Although the reaction consumes two moles of hydrogen per mole of acetic acid to produce one mole of ethanol, the actual molar ratio of hydrogen to acetic acid in the feed stream may vary from about 100:1 to 1:100, e.g., from 50:1 to 1:50, from 20:1 to 1:2, or from 18:1 to 2:1.

Contact or residence time can also vary widely, depending upon such variables as amount of acetic acid, catalyst, reactor, temperature, and pressure. Typical contact times range from a fraction of a second to more than several hours when a catalyst system other than a fixed bed is used, with preferred contact times, at least for vapor phase reactions, from 0.1 to 100 seconds.

The hydrogenation of acetic acid to form ethanol is preferably conducted in the presence of a hydrogenation catalyst. Exemplary catalysts are further described in U.S. Pat. Nos. 7,608,744 and 7,863,489, and U.S. Pub. Nos. 2010/50121114 and 2010/0197985, the entireties of which are incorporated herein by reference. In another embodiment, the catalyst comprises a Co/Mo/S catalyst of the type described in U.S. Pub. No. 2009/0069609, the entirety of which is incorporated herein by reference. In some embodiments the catalyst may be a bulk catalyst.

In one embodiment, the catalyst comprises a first metal selected from the group consisting of copper, iron, cobalt, nickel, ruthenium, rhodium, palladium, osmium, iridium, platinum, titanium, zinc, chromium, rhenium, molybdenum, and tungsten. Preferably, the first metal is selected from the group consisting of platinum, palladium, cobalt, nickel, and ruthenium.

As indicated above, in some embodiments, the catalyst further comprises a second metal, which typically would function as a promoter. If present, the second metal preferably is selected from the group consisting of copper, molybdenum, tin, chromium, iron, cobalt, vanadium, tungsten, palladium, platinum, lanthanum, cerium, manganese, ruthenium, rhenium, gold, and nickel. More preferably, the second metal is selected from the group consisting of copper, tin, cobalt, rhenium, and nickel.

In certain embodiments where the catalyst includes two or more metals, e.g., a first metal and a second metal, the first metal is present in the catalyst in an amount from 0.1 to 10 wt. %, e.g., from 0.1 to 5 wt. %, or from 0.1 to 3 wt. %. The second metal preferably is present in an amount from 0.1 to 20 wt. %, e.g., from 0.1 to 10 wt. %, or from 0.1 to 7.5 wt. %.

Preferred metal combinations for exemplary catalyst compositions include platinum/tin, platinum/ruthenium, platinum/rhenium, palladium/ruthenium, palladium/rhenium, cobalt/palladium, cobalt/platinum, cobalt/chromium, cobalt/ruthenium, cobalt/tin, silver/palladium, copper/palladium, copper/zinc, nickel/palladium, gold/palladium, ruthenium/rhenium, or ruthenium/iron.

The catalyst may also comprise a third metal selected from any of the metals listed above in connection with the first or second metal, so long as the third metal is different from the first and second metals. In preferred aspects, the third metal is selected from the group consisting of cobalt, palladium, ruthenium, copper, zinc, platinum, tin, and rhenium. When present, the total weight of the third metal preferably is from 0.05 to 20 wt. %, e.g., from 0.1 to 10 wt. %, or from 0.1 to 7.5 wt. %. In one embodiment, the catalyst may comprise platinum, tin and cobalt.

In addition to one or more metals, in some embodiments of the present invention the catalysts further comprise a support or a modified support. As used herein, the term "modified support" refers to a support that includes a support material and a support modifier, which adjusts the acidity of the support material.

The total weight of the support or modified support, based on the total weight of the catalyst, preferably is from 75 to 99.9 wt. %, e.g., from 78 to 97 wt. %, or from 80 to 95 wt. %. Preferred supports include silicaceous supports, such as silica, silica/alumina, a Group IIA silicate such as calcium metasilicate, pyrogenic silica, high purity silica, and mixtures thereof. Other supports may include, but are not limited to, iron oxide, alumina, titania, zirconia, magnesium oxide, carbon, graphite, high surface area graphitized carbon, activated carbons, and mixtures thereof. The support may be a modified support, and is present in an amount from 0.1 to 50 wt. %, e.g., from 0.2 to 25 wt. %, from 1 to 20 wt. %, or from 3 to 15 wt. %, based on the total weight of the catalyst.

In some embodiments, the support modifier may be an acidic modifier that increases the acidity of the catalyst. Suitable acidic support modifiers may be selected from the group consisting of: oxides of Group IVB metals, oxides of Group VB metals, oxides of Group VIB metals, oxides of Group VIIB metals, oxides of Group VIIIB metals, aluminum oxides, and mixtures thereof. Acidic support modifiers include those selected from the group consisting of $TiO_2$, $ZrO_2$, $Nb_2O_5$, $Ta_2O_5$, $Al_2O_3$, $B_2O_3$, $P_2O_5$, $Sb_2O_3$, $WO_3$, $MoO_3$, $Fe_2O_3$, $Cr_2O_3$, $V_2O_5$, $MnO_2$, $CuO$, $Co_2O_3$, and $Bi_2O_3$. Preferred support modifiers include oxides of tungsten, molybdenum, and vanadium.

In another embodiment, the support modifier may be a basic modifier that has a low volatility or no volatility. Such basic modifiers, for example, may be selected from the group consisting of: (i) alkaline earth metal oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. The basic support modifier may be selected from the group consisting of oxides and metasilicates of any of sodium, potassium, magnesium, calcium, scandium, yttrium, and zinc, as well as mixtures of any of the foregoing. In one embodiment, the basic support modifier is a calcium silicate, such as calcium metasilicate ($CaSiO_3$). The calcium metasilicate may be crystalline or amorphous.

Catalysts on a modified support may include one or more metals selected from the group consisting of platinum, palladium, cobalt, tin, and rhenium on a silica support, optionally modified by one or more modifiers selected from the group consisting of calcium metasilicate, and one or more oxides of tungsten, molybdenum, and/or vanadium.

The catalyst compositions suitable for use with the present invention preferably are formed through metal impregnation of the modified support, although other processes such as chemical vapor deposition may also be employed. Such impregnation techniques are described in U.S. Pat. Nos. 7,608,744 and 7,863,489 and U.S. Pub. No. 2010/0197985 referred to above, the entireties of which are incorporated herein by reference.

After the washing, drying and calcining of the catalyst is completed, the catalyst may be reduced in order to activate it. Reduction is carried out in the presence of a reducing gas, preferably hydrogen. The reducing gas is continuously passed over the catalyst at an initial ambient temperature that is increased up to 400° C. In one embodiment, the reduction is carried out after the catalyst has been loaded into the reaction vessel where the hydrogenation will be carried out.

In particular, the hydrogenation of acetic acid may achieve favorable conversion of acetic acid and favorable selectivity and productivity to ethanol. For purposes of the present invention, the term "conversion" refers to the amount of acetic acid in the feed that is converted to a compound other than acetic acid. Conversion is expressed as a percentage based on acetic acid in the feed. The conversion may be at least 40%, e.g., at least 50%, at least 60%, at least 70% or at least 80%. Although catalysts that have high conversions are desirable, such as at least 80% or at least 90%, in some embodiments a low conversion may be acceptable at high selectivity for ethanol.

Selectivity is expressed as a mole percent based on converted acetic acid. It should be understood that each compound converted from acetic acid has an independent selectivity and that selectivity is independent from conversion. For example, if 60 mole % of the converted acetic acid is converted to ethanol, we refer to the ethanol selectivity as 60%. Preferably, the catalyst selectivity to ethanol is at least 60%, e.g., at least 70%, or at least 80%. Preferred embodiments of the hydrogenation process also have low selectivity to undesirable products, such as methane, ethane, and carbon dioxide. The selectivity to these undesirable products preferably is less than 4%, e.g., less than 2% or less than 1%.

The term "productivity," as used herein, refers to the grams of a specified product, e.g., ethanol, formed during the hydrogenation based on the kilograms of catalyst used per hour. The productivity may range from 100 to 3,000 grams of ethanol per kilogram of catalyst per hour.

In various embodiments of the present invention, the crude ethanol product produced by the hydrogenation process, before any subsequent processing, such as purification and separation, will typically comprise unreacted acetic acid, ethanol and water. Exemplary compositional ranges for the crude ethanol product are provided in Table 1, excluding hydrogen. The "others" identified in Table 1 may include, for example, esters, ethers, aldehydes, ketones, alkanes, and carbon dioxide.

TABLE 1

CRUDE ETHANOL PRODUCT COMPOSITIONS

| Component | Conc. (wt. %) | Conc. (wt. %) | Conc. (wt. %) | Conc. (wt. %) |
|---|---|---|---|---|
| Ethanol | 5 to 72 | 15 to 72 | 15 to 70 | 25 to 65 |
| Acetic Acid | 0 to 90 | 0 to 50 | 0 to 35 | 0 to 15 |
| Water | 5 to 40 | 5 to 30 | 10 to 30 | 10 to 26 |
| Ethyl Acetate | 0 to 30 | 1 to 25 | 3 to 20 | 5 to 18 |
| Acetaldehyde | 0 to 10 | 0 to 3 | 0.1 to 3 | 0.2 to 2 |
| Others | 0.1 to 10 | 0.1 to 6 | 0.1 to 4 | — |

In one embodiment, the crude ethanol product of Table 1 may have low concentrations of acetic acid with higher conversion, and the acetic acid concentration may range from 0.01 wt. % to 20 wt. %, e.g., 0.05 wt. % to 15 wt. %, from 0.1 wt. % to 10 wt. % or from 1 wt. % to 5 wt. %. In embodiments having lower amounts of acetic acid, the conversion of acetic acid is preferably greater than 75%, e.g., greater than 85% or greater than 90%. In addition, the selectivity to ethanol may also be preferably high, and is preferably greater than 75%, e.g., greater than 85% or greater than 90%.

Ethanol Recovery

Figure 1:
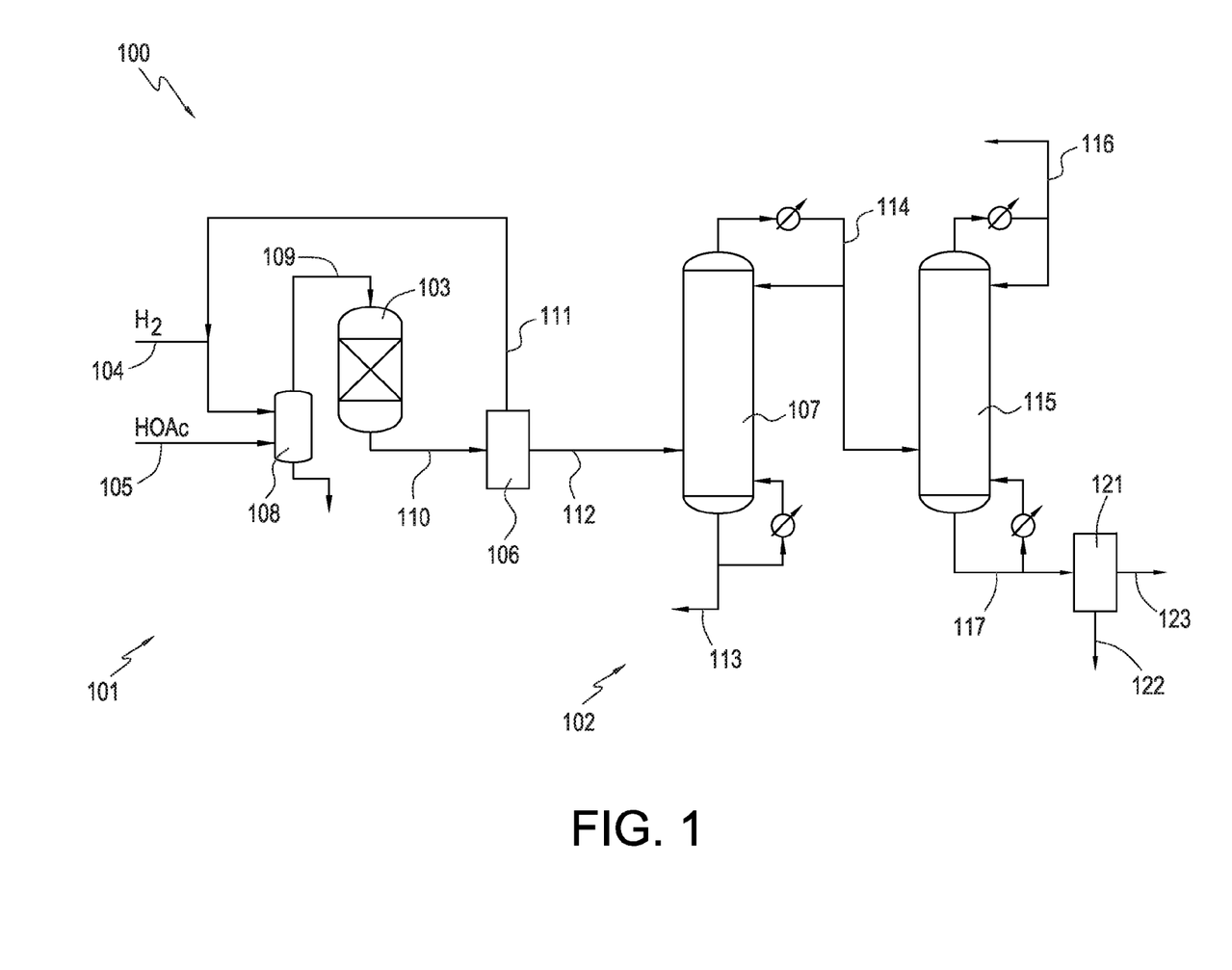
FIG. 1 is a schematic diagram of an ethanol production system having a water separation unit after a distillation column to separate organic impurities in accordance with one embodiment of the present invention.
Figure 2:
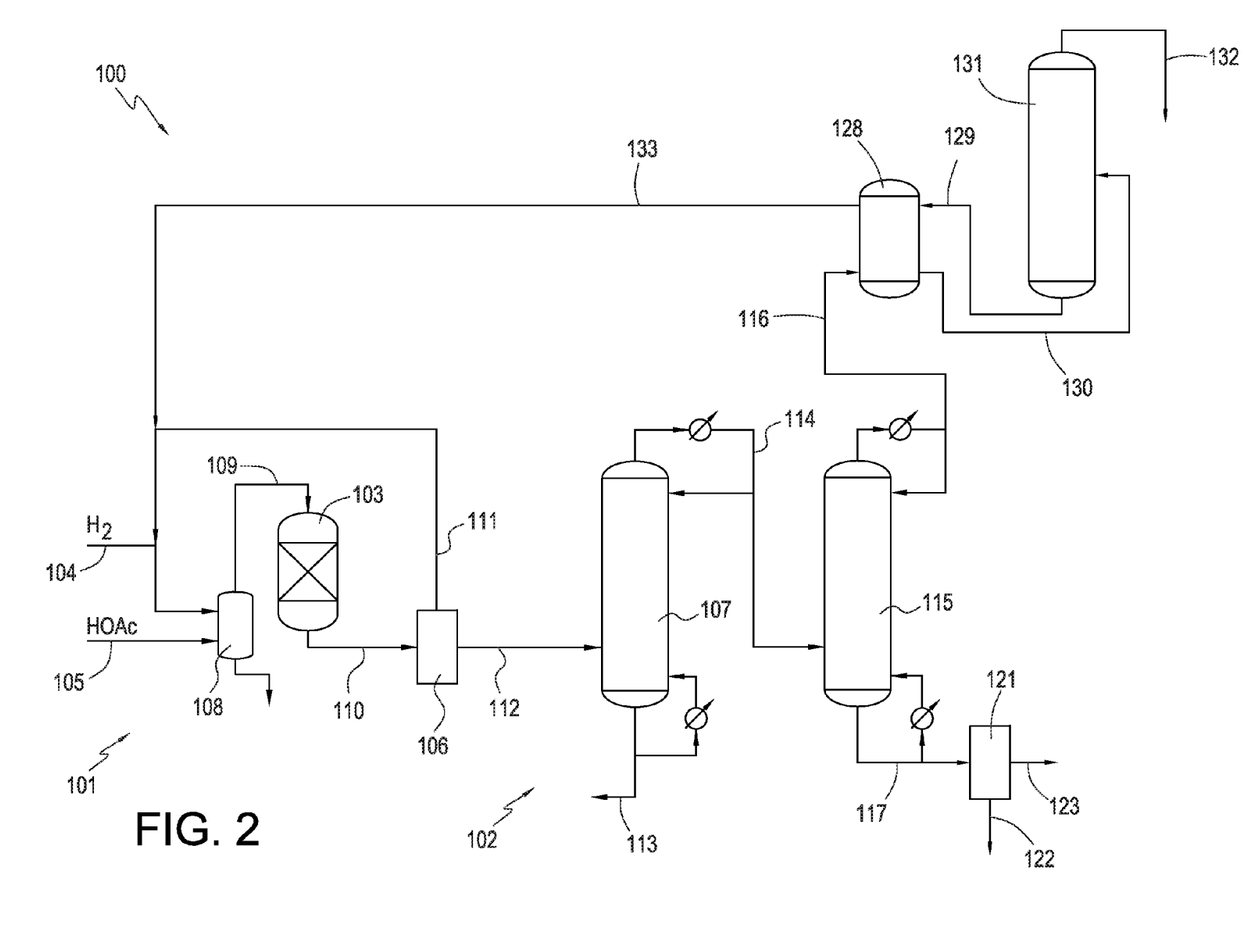
FIG. 2 is a schematic diagram of an ethanol production system for reducing the concentration of ethanol in the recycle streams in accordance with one embodiment of the present invention.

Exemplary ethanol recovery systems in accordance with embodiments of the present invention are shown in FIGS. 1 and 2. Each hydrogenation system 100 provides a suitable hydrogenation reactor and a process for separating ethanol from the crude reaction mixture according to an embodiment of the invention. System 100 comprises reaction zone 101 and separation zone 102. Reaction zone 101 comprises reactor 103, hydrogen feed line 104 and acetic acid feed line 105. Separation zone 102 comprises a separator 106, distillation columns 107 and 115 and a water separation unit 121. FIG. 2 also provides an extractor 128 for reducing the ethanol concentration recycled to reaction zone 101.

Hydrogen and acetic acid are fed to a vaporizer 108 via lines 104 and 105, respectively, to create a vapor feed stream in line 109 that is directed to reactor 103. In one embodiment, lines 104 and 105 may be combined and jointly fed to vaporizer 108. The temperature of the vapor feed stream in line 109 is preferably from 100° C. to 350° C., e.g., from 120° C. to 310° C. or from 150° C. to 300° C. Any feed that is not vaporized is removed from vaporizer 108 and may be recycled or discarded. In addition, although line 109 is shown as being directed to the top of reactor 103, line 109 may be directed to the side, upper portion, or bottom of reactor 103. Further modifications and additional components to reaction zone 101 and separation zone 102 are described below.

Reactor 103 contains the catalyst that is used in the hydrogenation of the carboxylic acid, preferably acetic acid. In one embodiment, one or more guard beds (not shown) may be used upstream of reactor 103 to protect the catalyst from poisons or undesirable impurities contained in the feed or return/recycle streams. Such guard beds may be employed in the vapor or liquid streams. Suitable guard bed materials may include, for example, carbon, silica, alumina, ceramic, or resins. In one aspect, the guard bed media is functionalized, e.g., silver functionalized, to trap particular species such as sulfur or halogens. During the hydrogenation process, a crude ethanol product is withdrawn, preferably continuously, from reactor 103 via line 110.

The crude ethanol product in line 110 may be condensed and fed to separator 106, which, in turn, provides a vapor stream 111 and a liquid stream 112. Suitable separators 106 include a flasher or a knockout pot. Separator 106 may operate at a temperature from 20° C. to 250° C., e.g., from 30° C. to 225° C. or from 60° C. to 200° C. The pressure of separator 106 may be from 50 kPa to 2500 kPa, e.g., from 75 kPa to 2250 kPa or from 100 to 2100 kPa. Optionally, the crude ethanol product in line 110 may pass through one or more membranes to separate hydrogen and/or other non-condensable gases.

Vapor stream 111 exiting separator 106 may comprise hydrogen and hydrocarbons, and may be purged and/or returned to reaction zone 101. As shown, vapor stream 111 is combined with hydrogen feed 104 and co-fed to vaporizer 108. In some embodiments, returned vapor stream 111 may be compressed before being combined with hydrogen feed 104.

Liquid stream 112 from separator 106 is withdrawn and pumped to the side of distillation column 107, also referred to as an "acid separation column." In one embodiment, the contents of liquid stream 112 are substantially similar to the crude ethanol product obtained from reactor 103, except that the composition has substantially no hydrogen, carbon dioxide, methane or ethane, which are removed by separator 106. Accordingly, liquid stream 112 may also be referred to as a crude ethanol product. Exemplary components of liquid stream 112 are provided in Table 2. It should be understood that liquid stream 112 may contain other components, not listed, such as components derived from the feed.

TABLE 2

| COLUMN FEED COMPOSITION (Liquid Stream 112) | | | |
|---|---|---|---|
|  | Conc. (wt. %) | Conc. (wt. %) | Conc. (wt. %) |
| Ethanol | 5 to 72 | 10 to 70 | 15 to 65 |
| Acetic Acid | <90 | 5 to 80 | 0 to 35 |
| Water | 5 to 40 | 5 to 30 | 10 to 26 |
| Ethyl Acetate | <30 | 1 to 25 | 3 to 20 |
| Acetaldehyde | <10 | 0.001 to 3 | 0.1 to 3 |
| Acetal | <5 | 0.01 to 5 | 0.01 to 3 |
| Acetone | <5 | 0.0005 to 0.05 | 0.001 to 0.03 |
| Other Esters | <5 | <0.005 | <0.001 |
| Other Ethers | <5 | <0.005 | <0.001 |
| Other Alcohols | <5 | <0.005 | <0.001 |

The amounts indicated as less than (<) in the tables throughout the present specification are preferably not present and if present may be present in trace amounts or in amounts greater than 0.0001 wt. %.

The "other esters" in Table 2 may include, but are not limited to, ethyl propionate, methyl acetate, isopropyl acetate, n-propyl acetate, n-butyl acetate or mixtures thereof. The "other ethers" in Table 2 may include, but are not limited to, diethyl ether, methyl ethyl ether, isobutyl ethyl ether or mixtures thereof. The "other alcohols" in Table 2 may include, but are not limited to, methanol, isopropanol, n-propanol, n-butanol or mixtures thereof. In one embodiment, liquid stream 112 may comprise propanol, e.g., isopropanol and/or n-propanol, in an amount from 0.001 to 0.1 wt. %, from 0.001 to 0.05 wt. % or from 0.001 to 0.03 wt. %. In should be understood that these other components may be carried through in any of the distillate or residue streams described herein and will not be further described herein, unless indicated otherwise.

Optionally, crude ethanol product in line 110 or in liquid stream 112 may be further fed to an esterification reactor, hydrogenolysis reactor, or combination thereof. An esterification reactor may be used to consume acetic acid present in the crude ethanol product to further reduce the amount of acetic acid to be removed. Hydrogenolysis may be used to convert ethyl acetate in the crude ethanol product to ethanol.

Liquid stream 112 may be introduced in the middle part of first column 107, e.g., lower half or middle third. In one embodiment, no entrainers are added to first column 107. In first column 107, water and unreacted acetic acid, along with any other heavy components, if present, are removed from liquid stream 112 and are withdrawn, preferably continuously, as residue in line 113. First column 107 also forms an overhead distillate, which is withdrawn in line 114, and which may be condensed and refluxed, for example, at a ratio of from 10:1 to 1:10, e.g., from 3:1 to 1:3 or from 1:2 to 2:1. In one embodiment, operating with a reflux ratio of less than 5:1 is preferred.

When column 107 is operated under about 170 kPa, the temperature of the residue exiting in line 113 preferably is from 90° C. to 130° C., e.g., from 95° C. to 120° C. or from 100° C. to 115° C. The base of column 107 may be maintained at a relatively low temperature to withdraw a residue stream comprising both water and acetic acid, thereby providing an energy efficiency advantage. The temperature of the distillate exiting in line 114 preferably is from 60° C. to 90° C., e.g., from 65° C. to 85° C. or from 70° C. to 80° C. In some embodiments, the pressure of first column 107 may range from 0.1 kPa to 510 kPa, e.g., from 1 kPa to 475 kPa or from 1 kPa to 375 kPa. Exemplary components of the distillate and residue compositions for first column 107 are provided in Table 3 below. It should also be understood that the distillate and residue may also contain other components, not listed, such as components derived from the feed. For convenience, the distillate and residue of first column 107 may also be referred to as the "first distillate" or "first residue." The distillates or residues of the other columns may also be referred to with similar numeric modifiers (second, third, etc.) in order to distinguish them from one another, but such modifiers should not be construed as requiring any particular separation order.

TABLE 3

FIRST COLUMN 107

| | Conc. (wt. %) | Conc. (wt. %) | Conc. (wt. %) |
|---|---|---|---|
| Distillate | | | |
| Ethanol | 20 to 90 | 30 to 85 | 45 to 85 |
| Water | 4 to 38 | 7 to 32 | 7 to 25 |
| Acetic Acid | <0.5 | 0.001 to 0.5 | 0.01 to 0.5 |
| Ethyl Acetate | <60 | 5 to 40 | 8 to 45 |
| Acetaldehyde | <10 | 0.001 to 5 | 0.01 to 4 |
| Acetal | <4.0 | <3.0 | <2.0 |
| Acetone | <0.05 | 0.001 to 0.03 | 0.01 to 0.025 |
| Residue | | | |
| Acetic Acid | <90 | 1 to 50 | 2.5 to 40 |
| Water | 30 to 100 | 45 to 90 | 60 to 90 |
| Ethanol | <1 | <0.9 | <0.5 |

In one embodiment, at high conversions of greater than 90%, acetic acid concentration in the residue may be less than 3 wt. %, e.g. from 0.5 to 3 wt. % or from 1 to 2.9 wt. %. Also, at lower conversions of acetic acid, less than 50%, the water concentration in the residue may be less than 30 wt. %, or less than 20 wt. %, while the acetic acid concentration in the residue may be greater than 40 wt. %, e.g., greater than 60 wt. % or greater than 80 wt. %.

Some species, such as acetals, may decompose in column 107 such that very low amounts, or even no detectable amounts, of acetals remain in the distillate or residue. In addition, an equilibrium reaction between acetic acid and ethanol or between ethyl acetate and water may occur in the crude ethanol product after it exits reactor 103. Depending on the concentration of acetic acid in the crude ethanol product, this equilibrium may be driven toward formation of ethyl acetate. This reaction may be regulated using the residence time and/or temperature of crude ethanol product.

Depending on the amount of water and acetic acid contained in the residue of first column 107, line 113 may be treated in one or more of the following processes. The following are exemplary processes for further treating first residue and it should be understood that any of the following may be used regardless of acetic acid concentration. When the residue comprises a majority of acetic acid, e.g., greater than 70 wt. %, the residue may be recycled to reactor 103 without any separation of the water. In one embodiment, the residue may be separated into an acetic acid stream and a water stream when the residue comprises a majority of acetic acid, e.g., greater than 50 wt. %. Acetic acid may also be recovered in some embodiments from first residue having a lower acetic acid concentration. The residue may be separated into the acetic acid and water streams by a distillation column or one or more membranes. If a membrane or an array of membranes is employed to separate the acetic acid from the water, the membrane or array of membranes may be selected from any suitable acid resistant membrane that is capable of removing a permeate water stream. The resulting acetic acid stream optionally is returned to reactor 103. The resulting water stream may be used as an extractive agent or to hydrolyze an ester-containing stream in a hydrolysis unit.

In other embodiments, for example where residue in line 113 comprises less than 50 wt. % acetic acid, possible options include one or more of: (i) returning a portion of the residue to reactor 103, (ii) neutralizing the acetic acid, (iii) reacting the acetic acid with an alcohol, or (iv) disposing of the residue in a waste water treatment facility. It also may be possible to separate a residue comprising less than 50 wt. % acetic acid using a weak acid recovery distillation column to which a solvent (optionally acting as an azeotroping agent) may be added. Exemplary solvents that may be suitable for this purpose include ethyl acetate, propyl acetate, isopropyl acetate, butyl acetate, vinyl acetate, diisopropyl ether, carbon disulfide, tetrahydrofuran, isopropanol, ethanol, and $C_3$-$C_{12}$ alkanes. When neutralizing the acetic acid, it is preferred that the residue in line 113 comprises less than 10 wt. % acetic acid. Acetic acid may be neutralized with any suitable alkali or alkaline earth metal base, such as sodium hydroxide or potassium hydroxide. When reacting acetic acid with an alcohol, it is preferred that the residue comprises less than 50 wt. % acetic acid. The alcohol may be any suitable alcohol, such as methanol, ethanol, propanol, butanol, or mixtures thereof. The reaction forms an ester that may be integrated with other systems, such as carbonylation production or an ester production process. Preferably, the alcohol comprises ethanol and the resulting ester comprises ethyl acetate. Optionally, the resulting ester may be fed to the hydrogenation reactor 103.

In some embodiments, when the residue comprises very minor amounts of acetic acid, e.g., less than 5 wt. %, the residue may be disposed of to a waste water treatment facility without further processing. The organic content, e.g., acetic acid content, of the residue beneficially may be suitable to feed microorganisms used in a waste water treatment facility.

The distillate in line 114 preferably comprises ethanol and optionally ethyl acetate, acetaldehyde, and water. In one embodiment, the weight ratio of water in the residue to the water in the distillate is greater than 1:1, e.g., greater than 2:1 or greater than 4:1. In addition, the weight ratio of acetic acid in the residue to acetic acid in the distillate is optionally greater than 10:1, e.g., greater than 15:1 or greater than 20:1. Preferably, the distillate in line 114 is substantially free of acetic acid and may contain, if any, only trace amounts of acetic acid.

The columns shown in FIGS. 1 and 2 may comprise any distillation column capable of performing the desired separation and/or purification. Each column preferably comprises a tray column having from 1 to 150 trays, e.g., from 10 to 100 trays, from 20 to 95 trays or from 30 to 75 trays. The trays may be sieve trays, fixed valve trays, movable valve trays, or any other suitable design known in the art. In other embodiments, a packed column may be used. For packed columns, structured packing or random packing may be employed. The trays or packing may be arranged in one continuous column or they may be arranged in two or more columns such that the vapor from the first section enters the second section while the liquid from the second section enters the first section, etc.

The associated condensers and liquid separation vessels that may be employed with each of the distillation columns may be of any conventional design and are simplified in the figures. Heat may be supplied to the base of each column or to a circulating bottom stream through a heat exchanger or reboiler. Other types of reboilers, such as internal reboilers, may also be used. The heat that is provided to the reboilers may be derived from any heat generated during the process that is integrated with the reboilers or from an external source such as another heat generating chemical process or a boiler. Although one reactor and one flasher are shown in the figures, additional reactors, flashers, condensers, heating elements, and other components may be used in various embodiments of the present invention. As will be recognized by those skilled in the art, various condensers, pumps, compressors, reboilers, drums, valves, connectors, separation vessels, etc., normally employed in carrying out chemical processes may also be combined and employed in the processes of the present invention.

The temperatures and pressures employed in the columns may vary. As a practical matter, pressures from 10 kPa to 3000 kPa will generally be employed in these zones although in some embodiments subatmospheric pressures or superatmospheric pressures may be employed. Temperatures within the various zones will normally range between the boiling points of the composition removed as the distillate and the composition removed as the residue. As will be recognized by those skilled in the art, the temperature at a given location in an operating distillation column is dependent on the composition of the material at that location and the pressure of column. In addition, feed rates may vary depending on the size of the production process and, if described, may be generically referred to in terms of feed weight ratios.

In FIG. 1, the distillate in line 114 comprises ethanol, water, and other organics such as ethyl acetate and/or acetaldehyde. In some embodiments, such distillate compositions may be possible at higher selectivities to ethanol, for example, selectivities of greater than 90%, greater than 95% or greater than 97%. The amount of water in the distillate of line 114 may be closer to the azeotropic amount of water, e.g., at least 4 wt. %, that forms with the ethanol/water azeotrope, preferably less than 20 wt. %, e.g., less than 12 wt. % or less than 7.5 wt. %.

Depending on the intended ethanol application, it may be desirable to remove water from the distillate in line 114. In some embodiments, removing substantially all of the water produces an anhydrous ethanol product suitable for fuel applications. Water may be removed from the distillate in line 114 using any of several different separation techniques. Particularly preferred techniques include the use of a distillation column, one or more membranes, one or more adsorption units or a combination thereof.

Although the distillate in line 114 in FIG. 1 primarily comprises ethanol and water, in most embodiments of the present invention the distillate in line 114 may further comprise ethyl acetate and acetaldehyde. As shown in FIG. 1, a second column 115, also referred to as the "light ends column," may remove ethyl acetate and acetaldehyde from distillate in line 114. In this embodiment, column 115 produces a light distillate in line 116 comprising ethyl acetate and acetaldehyde, and an ethanol residue in line 117 comprising ethanol and water.

In FIG. 1, distillate in line 114 is introduced to second column 115 preferably in the top part of column, e.g., top half or top third. Second column 115 may be a tray column or packed column. In one embodiment, second column 115 is a tray column having from 5 to 70 trays, e.g., from 15 to 50 trays or from 20 to 45 trays. As one example, when a 30 tray column is utilized in a column without water extraction, line 114 is introduced preferably at tray 2.

Optionally, light ends column 115 may be an extractive distillation column. Suitable extractive agents may include, for example, dimethylsulfoxide, glycerine, diethylene glycol, 1-naphthol, hydroquinone, N,N'-dimethylformamide, 1,4-butanediol; ethylene glycol-1,5-pentanediol; propylene glycol-tetraethylene glycol-polyethylene glycol; glycerine-propylene glycol-tetraethylene glycol-1,4-butanediol, ethyl ether, methyl formate, cyclohexane, N,N'-dimethyl-1,3-propanediamine, N,N'-dimethylethylenediamine, diethylene triamine, hexamethylene diamine and 1,3-diaminopentane, an alkylated thiopene, dodecane, tridecane, tetradecane, chlorinated paraffins, or a combination thereof. In another aspect, the extractive agent may be an aqueous stream comprising water. If the extraction agent comprises water, the water may be obtained from an external source or from an internal return/recycle line from one or more of the other columns or water separation units. Generally, the extractive agent is fed above the entry point of distillate in line 114. When extractive agents are used, a suitable recovery system, such as a further distillation column, may be used to remove the extractive agent and recycle the extractive agent.

Although the temperature and pressure of second column 115 may vary, when at about 20 kPa to 70 kPa, the temperature of the second residue exiting in line 117 preferably is from 30° C. to 75° C., e.g., from 35° C. to 70° C. or from 40° C. to 65° C. The temperature of the second distillate exiting in line 116 preferably is from 20° C. to 55° C., e.g., from 25° C. to 50° C. or from 30° C. to 45° C. Second column 115 may operate at a reduced pressure, near or at vacuum conditions, to further favor separation of ethyl acetate and ethanol. In other embodiments, the pressure of second column 115 may range from 0.1 kPa to 510 kPa, e.g., from 1 kPa to 475 kPa or from 1 kPa to 375 kPa. Exemplary components for the distillate and residue compositions for second column 115 are provided in Table 4, below. It should be understood that the distillate and residue may also contain other components, not listed, such as components derived from the feed.

TABLE 4

| LIGHT ENDS COLUMN 115 | | | |
| --- | --- | --- | --- |
|  | Conc. (wt. %) | Conc. (wt. %) | Conc. (wt. %) |
| Second Distillate | | | |
| Ethyl Acetate | 5 to 90 | 10 to 80 | 15 to 75 |
| Acetaldehyde | <60 | 1 to 40 | 1 to 35 |
| Ethanol | <45 | 0.001 to 40 | 0.01 to 35 |
| Water | <20 | 0.01 to 10 | 0.1 to 5 |
| Second Residue | | | |
| Ethanol | 40 to 99.5 | 50 to 95 | 60 to 90 |
| Water | <60 | 0.5 to 50 | 0.1 to 30 |
| Ethyl Acetate | <1 | 0.001 to 2 | 0.001 to 0.5 |
| Acetic Acid | <0.5 | <0.01 | 0.001 to 0.01 |

The weight ratio of ethanol in the second residue to ethanol in the second distillate preferably is at least 2:1, e.g., at least 5:1, at least 8:1, at least 10:1 or at least 15:1. The weight ratio of ethyl acetate in the second residue to ethyl acetate in the second distillate preferably is less than 0.7:1, e.g., less than 0.2:1 or less than 0.1:1. It should be understood that when an extractive agent is used, that the composition of the residue would also include the extractive agent. Preferably, the second residue comprises less than 0.01 wt. % ethyl acetate. The second residue may also comprise less than 35 wt. % water. The remaining water is removed using water separation unit 121.

In some embodiments, it may be desirable to have a vapor feed to a water separation unit. Preferably, a vapor portion of the ethanol residue in line 117 from the reboiler may be used. As shown in FIG. 1, a vapor portion of the ethanol residue in line 117 may be directed to water separation unit 121 to remove a water stream 122 from ethanol residue in line 117 thus producing an ethanol product stream 123 comprising 97 wt. %, 99.5 wt. % or more ethanol. Water separation unit 121 may remove at least 90% of the water from the treated portion of the ethanol residue in line 117, and more preferably from 95% to 99.99%. In one embodiment, ethanol product stream 123 has a lower water content than the ethanol residue in line 117. Ethanol product stream 123 may comprise less than 8 wt. % water, e.g., less than 4 wt. % water, less than 3 wt. % water or less than 1 wt. % water. Preferably at least 95% of the ethanol from the ethanol residue in line 117 is recovered by water separation unit 121 in ethanol product stream 123, and more preferably at least 99% of the ethanol. Water stream 122 may be combined with any other water stream from system 100 and preferably is removed from the system. The water stream may also comprise ethanol, in which case it may be desirable to feed all or a portion of the water stream back to column 115 for further ethanol recovery.

Water separator 121 may be an adsorption unit, membrane, molecular sieves, or a combination thereof. When membranes are used, there may be an array of membranes to remove water. In one embodiment, the adsorption unit may be a pressure swing adsorption (PSA) unit. The PSA unit may be operated at a temperature from 30° C. to 160° C., e.g., from 80° C. to 140° C., and a pressure of from 0.01 kPa to 550 kPa, e.g., from 1 kPa to 150 kPa. The PSA unit may comprise two to five beds.

Depending on the type of water separator 121, it may be necessary to compress the vapor portion of the ethanol residue in line 117. It particular, compression may be necessary when using membranes.

The second distillate in line 116, which comprises ethyl acetate and/or acetaldehyde, preferably is refluxed as shown in FIG. 1, for example, at a reflux ratio of from 1:30 to 30:1, e.g., from 1:5 to 5:1 or from 1:3 to 3:1. In one aspect, not shown, the second distillate or a portion thereof may be returned to reactor 103. In some embodiments, it may be advantageous to return a portion of second distillate to reactor 103. The ethyl acetate and/or acetaldehyde in the second distillate may be further reacted in hydrogenation reactor 103 or in a secondary reactor. The outflow from the secondary reactor may be fed to reactor 103 to produce additional ethanol or to a distillation column, such as columns, 107 or 115 to recover additional ethanol.

In some embodiments the second distillate in line 116 may also comprise up to 12 wt. % water. If all or a portion of the second distillate is returned to reactor 103, it may be necessary to remove water from line 116. The water from the second distillate in line 116 may be removed, for example, by an adsorption unit, one or more membranes, molecular sieves, extractive distillation, or a combination thereof. In some embodiments, an adsorption unit may also be used to remove a water from second distillate in line 116 to produce a distillate that comprising less than 1 wt. % water and more preferably less than 0.5 wt. % water.

In one embodiment, the second distillate in line 116 may be further separated to produce an acetaldehyde-containing stream and an ethyl acetate-containing stream. This may allow a portion of either the acetaldehyde-containing stream or ethyl acetate-containing stream to be recycled to reactor 103, while purging the other stream. The purge stream may be valuable as a source of either ethyl acetate and/or acetaldehyde.

As shown in FIG. 2, second distillate in line 116 is fed to extraction unit 128 to recover ethanol and reduce the ethanol concentration recycled to reactor 103. Extraction unit 128 may be a multi-stage extractor. In extraction unit 128, the second distillate is fed along with at least one extractive agent 129. In one embodiment, extractive agent 129 may be benzene, propylene glycol, and cyclohexane. Although water may be used, extractive agent 129 preferably does not form an azeotrope with ethanol. A suitable extractive agent 129 is preferably non-carcinogenic and non-hazardous. Preferably, extractive agent 129 extracts ethanol from the second distillate into extractant 130. Extractive agent 129 may be recovered in recovery column 131 and returned via line 130. The ethanol in line 132 may be combined with ethanol product stream 123. In one embodiment, raffinate 133 comprises less than 2 wt. % ethanol, e.g., less than 1 wt. % ethanol or less than 0.5 wt. % ethanol. Raffinate 133 may be returned to reaction zone 101. Preferably, raffinate 133 is deficient in ethanol with respect the second distillate in line 116. In some embodiments, at least a portion of raffinate 133 and/or at least a portion of extractant in line 130 may be purged from the system. Exemplary finished ethanol compositional ranges are provided below in Table 5.

TABLE 5

FINISHED ETHANOL COMPOSITIONS

| Component | Conc. (wt. %) | Conc. (wt. %) | Conc. (wt. %) |
|---|---|---|---|
| Ethanol | 75 to 99.5 | 80 to 99.5 | 85 to 99.5 |
| Water | <12 | 0.1 to 9 | 0.5 to 8 |
| Acetic Acid | <1 | <0.1 | <0.01 |
| Ethyl Acetate | <2 | <0.5 | <0.05 |
| Acetal | <0.05 | <0.01 | <0.005 |
| Acetone | <0.05 | <0.01 | <0.005 |
| Isopropanol | <0.5 | <0.1 | <0.05 |
| n-propanol | <0.5 | <0.1 | <0.05 |

The finished ethanol composition of the present invention preferably contains very low amounts, e.g., less than 0.5 wt. %, of other alcohols, such as methanol, butanol, isobutanol, isoamyl alcohol and other $C_4$-$C_{20}$ alcohols. In one embodiment, the amount of isopropanol in the finished ethanol composition is from 80 to 1,000 wppm, e.g., from 95 to 1,000 wppm, from 100 to 700 wppm, or from 150 to 500 wppm. In one embodiment, the finished ethanol composition is substantially free of acetaldehyde, optionally comprising less than 8 wppm acetaldehyde, e.g., less than 5 wppm or less than 1 wppm.

In some embodiments, when further water separation is used, the ethanol product may be withdrawn as a stream from the water separation unit as discussed above. In such embodiments, the ethanol concentration of the ethanol product may be higher than indicated in Table 5, and preferably is greater than 97 wt. % ethanol, e.g., greater than 98 wt. % or greater than 99.5 wt. %. The ethanol product in this aspect preferably comprises less than 3 wt. % water, e.g., less than 2 wt. % or less than 0.5 wt. %.

The finished ethanol composition produced by the embodiments of the present invention may be used in a variety of applications including applications as fuels, solvents, chemical feedstocks, pharmaceutical products, cleansers, sanitizers, hydrogen transport or consumption. In fuel applications, the finished ethanol composition may be blended with gasoline for motor vehicles such as automobiles, boats and small piston engine aircraft. In non-fuel applications, the finished ethanol composition may be used as a solvent for toiletry and cosmetic preparations, detergents, disinfectants, coatings, inks, and pharmaceuticals. The finished ethanol composition may also be used as a processing solvent in manufacturing processes for medicinal products, food preparations, dyes, photochemicals and latex processing.

The finished ethanol composition may also be used as a chemical feedstock to make other chemicals such as vinegar, ethyl acrylate, ethyl acetate, ethylene, glycol ethers, ethylamines, aldehydes, and higher alcohols, especially butanol. In the production of ethyl acetate, the finished ethanol composition may be esterified with acetic acid. In another application, the finished ethanol composition may be dehydrated to produce ethylene. Any known dehydration catalyst can be employed to dehydrate ethanol, such as those described in copending U.S. Pub. Nos. 2010/0030002 and 2010/0030001, the entire contents and disclosures of which are hereby incorporated by reference. A zeolite catalyst, for example, may be employed as the dehydration catalyst. Preferably, the zeolite has a pore diameter of at least about 0.6 nm, and preferred zeolites include dehydration catalysts selected from the group consisting of mordenites, ZSM-5, a zeolite X and a zeolite Y. Zeolite X is described, for example, in U.S. Pat. No. 2,882,244 and zeolite Y in U.S. Pat. No. 3,130,007, the entireties of which are hereby incorporated herein by reference.

In order that the invention disclosed herein may be more efficiently understood, an example is provided below. It should be understood that these examples are for illustrative purposes only and is not to be construed as limiting the invention in any manner.

While the invention has been described in detail, modifications within the spirit and scope of the invention will be readily apparent to those of skill in the art. In addition, it should be understood that aspects of the invention and portions of various embodiments and various features recited herein and/or in the appended claims may be combined or interchanged either in whole or in part. In the foregoing descriptions of the various embodiments, those embodiments which refer to another embodiment may be appropriately combined with one or more other embodiments, as will be appreciated by one of skill in the art. Furthermore, those of ordinary skill in the art will appreciate that the foregoing description is by way of example only, and is not intended to limit the invention.

We claim:

1. A process for producing ethanol, comprising the steps of:
   hydrogenating acetic acid from an acetic acid feed stream in a reactor to form a crude ethanol product;
   separating at least a portion of the crude ethanol product in a column into a first distillate comprising ethanol, ethyl acetate, and at least 5 wt. % water, and a first residue comprising acetic acid and water, wherein a substantial portion of the water in the crude ethanol product that is fed to the column is removed in the first residue;
   separating at least a portion of the first distillate into a first stream comprising ethanol and water, and a second stream comprising ethyl acetate; and
   removing water from the first stream using a water removal unit to form an ethanol product stream, provided that no water is removed from the first distillate prior to separating the at least a portion of the first distillate.

2. The process of claim 1, wherein from 30 to 90% of the water in the crude ethanol product is removed in the first residue stream.

3. The process of claim 1, wherein at least 50% of the water in the crude ethanol product is removed in the first residue stream.

4. The process of claim 1, wherein a vapor portion of the second residue is fed to the water removal unit.

5. The process of claim 1, wherein the water removal unit is selected from the group consisting of adsorption unit, membrane, molecular sieves, and combinations thereof.

6. The process of claim 1, wherein the first distillate comprises less than 0.5 wt. % acetic acid.

7. The process of claim 1, wherein the second residue comprises less than 0.01 wt. % ethyl acetate.

8. The process of claim 1, wherein the second residue comprises less than 35 wt. % water.

9. The process of claim 1, wherein the ethanol product stream has a lower water content than the second residue.

10. The process of claim 1, wherein the ethanol product stream comprises less than 4 wt. % water.

11. The process of claim 1, wherein the acetic acid is formed from methanol and carbon monoxide, wherein each of the methanol, the carbon monoxide, and hydrogen for the hydrogenating step is derived from syngas, and wherein the syngas is derived from a carbon source selected from the group consisting of natural gas, oil, petroleum, coal, biomass, and combinations thereof.

12. The process of claim 1, further comprising recovering acetic acid from the first residue and returning at least a portion of the recovered acetic acid to the reactor.

13. The process of claim 1, wherein the first residue comprises 0.5 to 10 wt. % acetic acid, the process further comprising the step of neutralizing or reacting the acetic acid from the first residue.

14. The process of claim 1, further comprising returning at least a portion of the second distillate to the reactor.

15. The process of claim 1, further comprising extracting the second distillate to provide a raffinate that is deficient in ethanol.

16. A process for producing ethanol, comprising the steps of:
   hydrogenating acetic acid from an acetic acid feed stream in a reactor to form a crude ethanol product;
   separating at least a portion of the crude ethanol product in a column into a first distillate comprising ethanol, ethyl acetate, and at least 5 wt. % water, and a first residue comprising acetic acid and water, wherein a substantial portion of the water in the crude ethanol product that is fed to the column is removed in the first residue;
   separating at least a portion of the first distillate in a second distillation column into a second residue comprising ethanol and water, and a second distillate comprising ethyl acetate; and
   removing water from a vapor portion of the second residue using a water removal unit to form the ethanol product stream.

17. A process for producing ethanol, comprising the steps of:
   hydrogenating acetic acid from an acetic acid feed stream in a reactor to form a crude ethanol product;
   separating at least a portion of the crude ethanol product in a column into a first distillate comprising ethanol, ethyl acetate, and at least 5 wt. % water, and a first residue comprising acetic acid and water, wherein a substantial portion of the water in the crude ethanol product that is fed to the column is removed in the first residue;

separating at least a portion of the first distillate in a second distillation column into a second residue comprising ethanol and water, and a second distillate comprising ethyl acetate and ethanol; and extracting ethanol from the second distillate to provide a raffinate that is deficient in ethanol.

18. The process of claim 17, wherein the raffinate is returned to the reactor.

19. The process of claim 17, wherein the raffinate has an ethanol concentration that is less than the ethanol concentration of the second distillate.

20. The process of claim 17, wherein the raffinate comprises less than 2 wt. % ethanol.

21. The process of claim 17, wherein the extracted ethanol is combined with the second residue.

22. The process of claim 17, wherein at least 80% of the ethanol in the second distillate is recovered through extraction.

* * * * *